United States Patent

Zipplies et al.

Patent Number: 5,268,351
Date of Patent: Dec. 7, 1993

[54] N-HETEROCYCLOMETHYL-SPIROHETEROCYCLES AND FUNGICIDES CONTAINING THEM

[75] Inventors: Matthias Zipplies, Hirschberg; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 924,929

[22] Filed: Aug. 5, 1992

Related U.S. Application Data

[62] Division of Ser. No. 565,099, Aug. 10, 1990, Pat. No. 5,175,295.

[30] Foreign Application Priority Data

Aug. 12, 1989 [DE] Fed. Rep. of Germany ....... 3926769
Dec. 19, 1989 [DE] Fed. Rep. of Germany ....... 3941870

[51] Int. Cl.$^5$ .................. C07D 317/72; A01N 43/40
[52] U.S. Cl. ................................... 504/130; 546/15; 546/139
[58] Field of Search ................ 546/139, 15; 504/130

[56] References Cited

U.S. PATENT DOCUMENTS

4,851,405 7/1989 Kramer .................. 514/212

FOREIGN PATENT DOCUMENTS

278352  5/1989 European Pat. Off. .
281842  5/1989 European Pat. Off. .
349247  1/1990 European Pat. Off. .
0359979 3/1990 European Pat. Off. .

OTHER PUBLICATIONS

Chemical Abstracts Service 113:6355, 1990, (of Svendsen EP 349247).
Chemical Abstracts Service 110:23868t, 1989, (of DE 3735555, equiv. to U.S. Pat. No. 4,851,405).

Primary Examiner—Marianne M. Cintins
Assistant Examiner—Catherine S. Kilby Scalzo
Attorney, Agent, or Firm—Oblon, Spivak, McClelland, Maier & Neustadt

[57] ABSTRACT

N-Heterocyclomethylspiroheterocycles of the general formula I

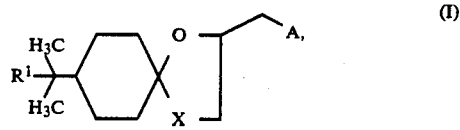

(I)

where
A is a radical II, III or IV

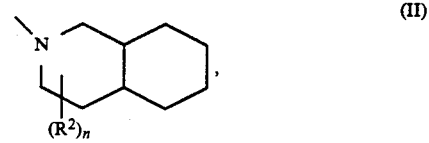

(II)

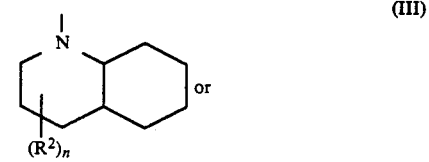

(III)

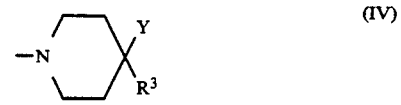

(IV)

$R^2$ is $CH_3$, OH or $OCH_3$,
n is from 0 to 3,
$R^3$ is hydroxyl, acyloxy, alkoxy, unsubstituted or substituted benzoyloxy, unsubstituted or substituted benzyloxy, unsubstituted or substituted alkyl or unsubstituted or substituted alkenyl, unsubstituted or substituted aryl,
X is oxygen, sulfur or methylene,
Y is hydrogen or hydroxyl, and
$R^1$ is hydrogen, alkyl or unsubstituted or substituted cyclohexyl or unsubstituted or substituted phenyl, their addition salts with acids, and fungicides containing these compounds.

7 Claims, No Drawings

N-HETEROCYCLOMETHYLSPIROHETEROCYCLES AND FUNGICIDES CONTAINING THEM

This is a division of application Ser. No. 07/565,099, filed on Aug. 10, 1990, now U.S. Pat. No. 5,175,295.

The present invention relates to N-heterocyclomethylspiroheterocycles, fungicides containing them and methods for controlling fungi using these compounds.

It is known that piperidinomethylspiroheterocycles, for example the compound IX (EP 281 842), have fungicidal properties.

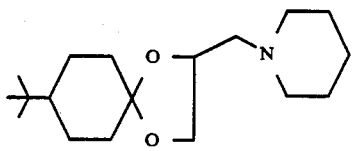

(IX)

However, the activity of this known compound is unsatisfactory, particularly at low application rates and concentrations.

We have found that N-heterocyclomethylspiroheterocycles of the general formula I

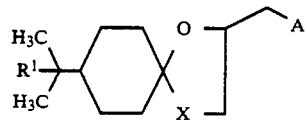

(I)

where
A is a radical II, III or IV

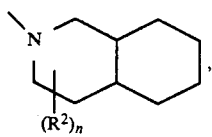

(II)

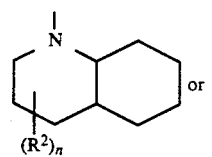

(III) or

(IV)

$R^2$ is $CH_3$, OH or $OCH_3$,
n is from 0 to 3,
$R^3$ is hydroxyl, acyloxy, alkoxy, unsubstituted or substituted benzoyloxy, unsubstituted or substituted benzyloxy, unsubstituted or substituted alkyl or unsubstituted or substituted alkenyl, where the substituents are unsubstituted or substituted aryl, hydroxyl, acyloxy, alkoxy or benzyloxy, or
$R^3$ is aryl which is unsubstituted or substituted by halogen or by alkyl,
X is oxygen, sulfur or methylene,
Y is hydrogen or hydroxyl and
$R^1$ is hydrogen, alkyl or unsubstituted or substituted cyclohexyl or unsubstituted or substituted phenyl, and their addition salts with acids have an excellent fungicidal action against phytopathogenic fungi.

Particularly preferred for the purposes of the present invention are N-heterocyclomethylspiroheterocycles of the general formula I, where
A is a radical II, III or IV, as claimed in claim 1,
n is 0 or 1,
$R^2$ is $CH_3$, OH or $OCH_3$,
$R^3$ is hydroxyl, $C_1$-$C_4$-acyloxy, $C_1$-$C_8$-alkoxy or benzoyloxy which is unsubstituted or monosubstituted to trisubstituted by halogen or $C_1$-$C_4$-alkyl, benzyloxy which is unsubstituted or monosubstituted to trisubstituted by halogen or $C_1$-$C_4$-alkyl, $C_1$-$C_8$-alkyl which is unsubstituted or substituted by OH, aryl (phenyl), $C_1$-$C_4$-acyloxy, benzoyloxy, $C_1$-$C_8$-alkoxy or benzyloxy, or $C_3$- or $C_4$-alkenyl which is unsubstituted or substituted by OH, aryl (phenyl), $C_1$-$C_4$-acyloxy, benzoyloxy, $C_1$-$C_8$-alkoxy or benzyloxy, or phenyl which is unsubstituted or substituted by 1 to 3 halogen or $C_1$-$C_4$-alkyl radicals,
X is oxygen, sulfur or methylene,
Y is hydrogen or hydroxyl,
$R^1$ is hydrogen, straight-chain or branched alkyl of 1 to 6 carbon atoms or phenyl which is unsubstituted or monosubstituted to trisubstituted by identical or different alkyl radicals of 1 to 4 carbon atoms or halogen radicals, or cyclohexyl which is unsubstituted or monosubstituted to trisubstituted by identical or different $C_1$-$C_4$-alkyl or halogen radicals, and their addition salts with acids.

Surprisingly, the novel compounds have a better fungicidal action than the known compound of the formula IV, which is similar to the novel compounds.

Formula I gives the general definition of the novel compounds.

In the formula,
A is, for example, the trans- or cis-perhydroisoquinolyl or the trans- or cis-perhydroquinolyl radical or a mixture of the corresponding cis/trans isomers or is the piperidinyl radical,
$R^2$ is methyl, hydroxyl or methoxy,
n is, for example, 0 or 1,
$R^3$ is, for example, hydroxyl, acetoxy, benzoyloxy, $C_1$-$C_4$-alkoxy, such as methoxy, ethoxy, isopropoxy or tert-butoxy, benzyloxy, $C_1$-$C_4$-alkyl, such as methyl, ethyl, propyl, isopropyl, sec-butyl, tert-butyl or neopentyl, phenyl, halophenyl, such as 4-fluorophenyl, $C_1$-$C_4$-alkylphenyl, such as 4-tert-butylphenyl, hydroxymethyl, $C_1$-$C_4$-alkoxymethyl, such as methoxymethyl, ethoxymethyl or tert-butoxymethyl, acetoxymethyl, pivaloyloxymethyl, benzyloxymethyl, benzyl, hydroxyethyl, methoxyethyl, tert-butoxyethyl, acetoxyethyl or benzoyloxyethyl,
X is, for example, oxygen, sulfur or methylene, oxygen being preferred,
Y is hydrogen or hydroxyl, hydrogen being preferred, and
$R^1$ is, for example, hydrogen, methyl, ethyl, 2,2-dimethylpropyl, cyclohexyl or phenyl, methyl being preferred.

Other preferred novel compounds are the adducts of acids and compounds of the formula I in which A, n, X, Y, $R^1$, $R^2$ and $R^3$ have the abovementioned meanings.

Such acids are, for example, mineral acids, such as hydrochloric acid, hydrobromic acid, phosphoric acid, sulfuric acid or nitric acid, or carboxylic acids, such as formic acid, acetic acid, oxalic acid, malonic acid, lactic acid, malic acid, succinic acid, tartaric acid, citric acid, salicylic acid, p-toluenesulfonic acid or dodecylbenzenesulfonic acid or generally proton-acidic compounds, e.g. saccharin. Salts with plant-tolerated acids are preferred (plant-tolerated salts).

The novel compounds of the formula I may be obtained in the preparation as mixtures of stereoisomers (E/Z isomers, diastereomers, enantiomers), which can be separated into the individual components in a conventional manner, for example by crystallization or chromatography. Both the individual isomers and mixtures thereof can be used as fungicides and form the subject of the invention.

The novel compounds of the formula I can be prepared in a conventional manner (cf. EP 281 842 and 278 352) by reacting a substituted spiroheterocycle of the general formula V

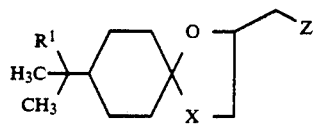  (V)

where R¹ and X have the abovementioned meanings and Z is an electron-attracting, nucleophilically replaceable leaving group, with a heterocycloamine derivative of the general formula VI/VII/VIII

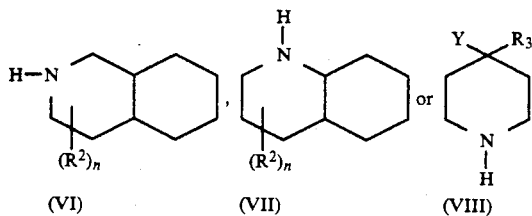

(VI)  (VII)  (VIII)

where R², R³, Y and n have the abovementioned meanings, in the presence or absence of a diluent and in the presence or absence of an auxiliary base.

The substituted spiroheterocycles of the general formula (V) are known or can be prepared in a conventional manner (cf. EP 281 842 or 278 352 and the literature cited therein). Some of the perhydro(iso)quinoline derivatives of the general formulae VI/VII are known; those which are unknown can be prepared by conventional processes, for example by catalytic hydrogenation of (iso)quinoline derivatives. The piperidine derivatives of the general formula VIII are substantially known or can be prepared by conventional processes, by hydrogenation of pyridine derivatives or derivatization of 4-hydroxypiperidines or 4-hydroxyalkylpiperidines.

PREPARATION EXAMPLE 1

8-tert-Butyl-2-(perhydroisoquinolinomethyl)-1,4-dioxaspiro[4,5]decane (compound No. 1.1)

10 g (34 mmol) of 8-tert-butyl-2-bromomethyl-1,4-dioxaspiro[4,5]decane, 5.2 g (37.4 mmol) of perhydroisoquinoline (isomer mixture) and 4.7 g (34 mmol) of potassium carbonate in 100 ml of acetonitrile were refluxed for 16 hours. The solvent was distilled off under reduced pressure, the resulting residue was taken up with dilute 5% strength NaOH and methyl tert-butyl ether, and the organic phase was washed twice with water, dried over Na₂SO₄ and evaporated down under reduced pressure. Fractionation of the crude product under reduced pressure gave 4.9 g of compound 1.1 (bp. 170° C., 0.5 mbar). Preparation of the starting compound

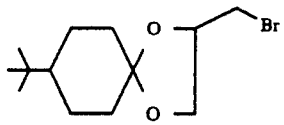

30.15 g (120 mmol) of tin(IV) chloride were added dropwise to 115.5 g (750 mmol) of 4-tert-butylcyclohexanone in 700 ml of absolute dichloromethane at 5° C., followed by the dropwise addition of 205.5 g (1.5 mol) of epibromohydrin

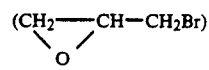

in 370 ml of absolute dichloromethane in the course of 5 hours. The mixture was stirred overnight at room temperature (20° C.), hydrolyzed with a solution of 42 g of KOH in 180 ml of water while cooling, and worked up in a conventional manner. Distillation of the crude product (279 g) under reduced pressure gave 169 g (77.5%) of 8-tert-butyl-2-bromomethyl-1,4-dioxaspiro[4,5]decane of boiling point 110° C./0.2 mbar.

PREPARATION EXAMPLE 2

8-tert-Butyl-2-(4-tert-butylpiperidinomethyl)-1,4-dioxaspiro[4,5]decane (compound No. 2.5)

17.4 g (123.6 mmol) of 4-tert-butylpiperidine, 9.0 g (30.9 mmol) of 8-tert-butyl-2-bromomethyl-1,4-dioxaspiro[4,5]decane (cis/trans mixture) and 4.3 g (30.9 mmol) of potassium carbonate in 100 ml of absolute dimethylformamide were heated at 150° C. for 8 hours. Some of the solvent was distilled off under reduced pressure, the residue was taken up with dilute aqueous sodium hydroxide solution/methylene chloride and the solution was worked up in a conventional manner.

The crude product was distilled under reduced pressure to give 4.5 g of a product of boiling point 190° C. (0.3 mbar) (diastereomer mixture).

The other novel compounds listed in Tables 1 and 2 can be prepared in a similar manner.

8-(Prop-2-yl)-2-perhydroisoquinolinomethyl)-1,4-dioxaspiro[4,5] decane is another compound of the invention.

TABLE 1

| | | (I) |
|---|---|---|

| No. | A | X | R¹ | m.p./b.p. [°C.] IR (film) [cm⁻¹] |
|---|---|---|---|---|
| 1.1 | (perhydroisoquinolinyl group) | O | CH₃ | 170° C./ 0.5 mbar |

TABLE 1-continued $$\text{(I)}$$

Structure: R¹(CH₃)(CH₃)C-cyclohexyl-C(X)(O-CH₂-CH(A))

| No. | A | X | R¹ | m.p./b.p. [°C] IR (film) [cm⁻¹] |
|---|---|---|---|---|
| 1.2 | N-methyl decahydroisoquinoline | CH₂ | CH₃ | |
| 1.3 | N-methyl decahydroisoquinoline | O | C₂H₅ | |
| 1.4 | N-methyl decahydroisoquinoline | O | cyclohexyl | |
| 1.5 | N-methyl decahydroisoquinoline | O | phenyl | |
| 1.6 | N-methyl decahydroisoquinoline | O | 2-methyl-propyl | |
| 1.7 | N-methyl decahydroquinoline | O | CH₃ | |
| 1.8 | N-methyl decahydroquinoline | O | C₂H₅ | |
| 1.9 | N-methyl decahydroquinoline | CH₂ | CH₃ | |
| 1.10 | N-methyl-CH₃-decahydroisoquinoline | O | CH₃ | |
| 1.11 | N-methyl-CH₃-decahydroisoquinoline | O | C₂H₅ | |
| 1.12 | H₃C-substituted N-methyl decahydroisoquinoline | O | CH₃ | |
| 1.13 | CH₃-substituted decahydroquinoline | O | CH₃ | |
| 1.14 | H₃C-substituted decahydroquinoline | O | CH₃ | |
| 1.15 | H₃C-substituted decahydroquinoline | O | CH₃ | |
| 1.16 | H₃C-, CH₃-disubstituted decahydroquinoline | O | CH₃ | |
| 1.17 | CH₃-substituted decahydroquinoline | O | CH₃ | |
| 1.18 | CH₃-substituted decahydroquinoline | O | CH₃ | |
| 1.19 | CH₃-substituted decahydroquinoline | O | CH₃ | |
| 1.20 | CH₃-substituted decahydroquinoline | O | CH₃ | |
| 1.21 | decahydroisoquinoline (trans isomer) | O | CH₃ | |

TABLE 1-continued
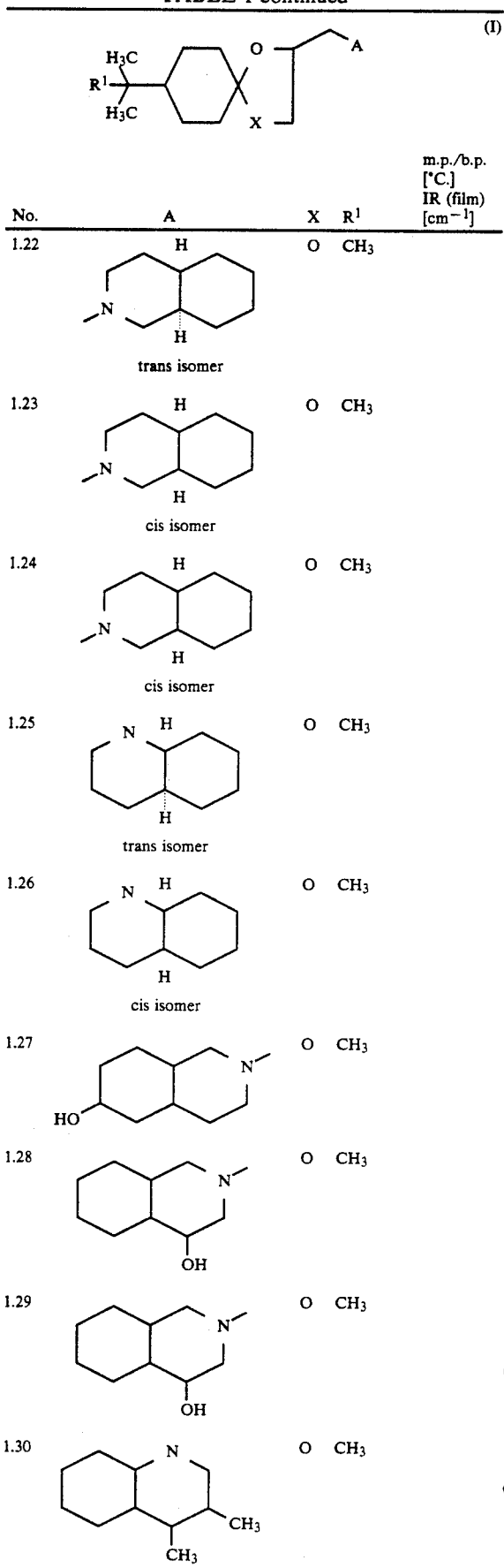
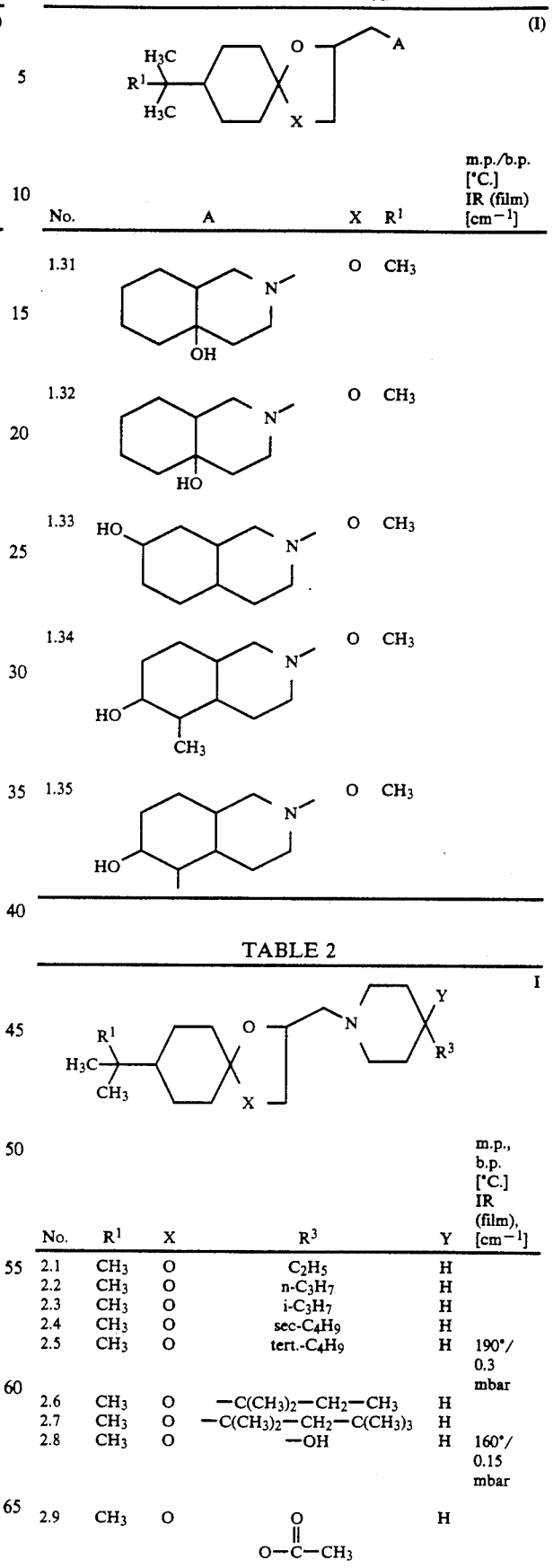
TABLE 2
| No. | R¹ | X | R³ | Y | m.p., b.p. [°C.] IR (film), [cm$^{-1}$] |
|---|---|---|---|---|---|
| 2.1 | CH$_3$ | O | C$_2$H$_5$ | H | |
| 2.2 | CH$_3$ | O | n-C$_3$H$_7$ | H | |
| 2.3 | CH$_3$ | O | i-C$_3$H$_7$ | H | |
| 2.4 | CH$_3$ | O | sec-C$_4$H$_9$ | H | |
| 2.5 | CH$_3$ | O | tert.-C$_4$H$_9$ | H | 190°/0.3 mbar |
| 2.6 | CH$_3$ | O | —C(CH$_3$)$_2$—CH$_2$—CH$_3$ | H | |
| 2.7 | CH$_3$ | O | —C(CH$_3$)$_2$—CH$_2$—C(CH$_3$)$_3$ | H | |
| 2.8 | CH$_3$ | O | —OH | H | 160°/0.15 mbar |
| 2.9 | CH$_3$ | O | O—C(=O)—CH$_3$ | H | |

TABLE 2-continued

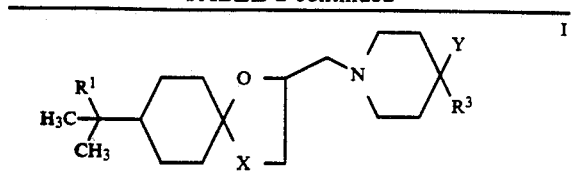

I

| No. | R¹ | X | R³ | Y | m.p., b.p. [°C.] IR (film), [cm⁻¹] |
|---|---|---|---|---|---|
| 2.10 | CH₃ | O | O–C(=O)–C₂H₅ | H | |
| 2.11 | CH₃ | O | O–C(=O)–C₆H₅ | H | |
| 2.12 | CH₃ | O | O–C(=O)–C(CH₃)₃ | H | |
| 2.13 | CH₃ | O | –OCH₃ | H | |
| 2.14 | CH₃ | O | –OC₂H₅ | H | |
| 2.15 | CH₃ | O | –O–CH(CH₃)₂ | H | |
| 2.16 | CH₃ | O | –O–C(CH₃)₃ | H | |
| 2.17 | CH₃ | O | –CH₂–OH | H | |
| 2.18 | CH₃ | O | –CH₂O–CH₃ | H | |
| 2.19 | CH₃ | O | –CH₂–O–C₂H₅ | H | |
| 2.20 | CH₃ | O | –CH₂–O–C(=O)–CH₃ | H | |
| 2.21 | CH₃ | O | –CH₂–CH₂–OH | H | |
| 2.22 | CH₃ | O | –CH₂–CH₂–OCCH₃ (O) | H | |
| 2.23 | CH₃ | O | C₆H₅ | H | |
| 2.24 | CH₃ | O | C₆H₅ | OH | 200°/0.1 mbar |
| 2.25 | CH₃ | O | 4-F–C₆H₅ | OH | |
| 2.26 | CH₃ | O | C₆H₅–CH₂– | H | oil |
| 2.27 | CH₃ | O | C₆H₅(CH₂)₂– | H | |
| 2.28 | CH₃ | O | C₆H₅(CH₂)₃– | H | oil; 2939, 1465, 1323, 1195, 1103 cm⁻¹ |
| 2.29 | CH₃ | O | 4-t-C₄H₉–C₆H₄– | H | |
| 2.30 | CH₃ | S | i-C₃H₇ | H | |
| 2.31 | CH₃ | S | tert.-C₄H₉ | H | |
| 2.32 | CH₃ | S | C(CH₃)₂–CH₂CH₃ | H | |
| 2.33 | CH₃ | S | OH | H | |
| 2.34 | CH₃ | S | O–CH₃ | H | |
| 2.35 | CH₃ | S | O–C₂H₅ | H | |
| 2.36 | CH₃ | S | O–C(=O)CH₃ | H | |
| 2.37 | CH₃ | S | O–C(=O)–C(CH₃)₃ | H | |
| 2.38 | CH₃ | S | C₆H₅ | H | |
| 2.39 | CH₃ | S | C₆H₅ | OH | |
| 2.40 | CH₃ | CH₂ | i-C₃H₇ | H | |
| 2.41 | CH₃ | CH₂ | sec-C₄H₉ | H | |
| 2.42 | CH₃ | CH₂ | tert.-C₄H₉ | H | |
| 2.43 | CH₃ | CH₂ | C(CH₃)₂–CH₂CH₃ | H | |
| 2.44 | CH₃ | CH₂ | C(CH₃)₂–CH₂–C(CH₃)₃ | H | |
| 2.45 | CH₃ | CH₂ | OH | H | |
| 2.46 | CH₃ | CH₂ | O–CH₃ | H | |
| 2.47 | CH₃ | CH₂ | O–C₂H₅ | H | |
| 2.48 | CH₃ | CH₂ | O–C(=O)–CH₃ | H | |
| 2.49 | CH₃ | CH₂ | O–C(=O)–C(CH₃)₃ | H | |
| 2.50 | CH₃ | CH₂ | CH₂–OH | H | |
| 2.51 | CH₃ | CH₂ | CH₂–OCH₃ | H | |
| 2.52 | CH₃ | CH₂ | CH₂–O–C₂H₅ | H | |
| 2.53 | CH₃ | CH₂ | CH₂–O–C(=O)CH₃ | H | |
| 2.54 | CH₃ | CH₂ | CH₂CH₂OH | H | |
| 2.55 | CH₃ | CH₂ | CH₂CH₂–OCH₃ | H | |
| 2.56 | CH₃ | CH₂ | CH₂CH₂–OC(=O)CH₃ | H | |
| 2.57 | CH₃ | CH₂ | C₆H₅ | H | |
| 2.58 | CH₃ | CH₂ | C₆H₅ | OH | |
| 2.59 | CH₃ | CH₂ | C₆H₅–CH₂ | H | |
| 2.60 | CH₃ | CH₂ | C₆H₅–(CH₂)₃– | H | |
| 2.61 | CH₃ | CH₂ | 4-tert.-C₄H₉–C₆H₄ | H | |
| 2.62 | H | O | C₂H₅ | H | |
| 2.63 | H | O | i-C₃H₇ | H | |
| 2.64 | H | O | t-C₄H₉ | H | |
| 2.65 | H | O | –OH | H | |
| 2.66 | H | O | –O–CH₃ | H | |
| 2.67 | H | O | –O–C(=O)CH₃ | H | |
| 2.68 | H | O | C₆H₅ | H | |
| 2.69 | H | O | C₆H₅ | OH | |
| 2.70 | H | O | C₆H₅CH₂ | H | |
| 2.71 | C₂H₅ | O | C₂H₅ | H | |
| 2.72 | C₂H₅ | O | n-C₃H₇ | H | |
| 2.73 | C₂H₅ | O | i-C₃H₇ | H | |
| 2.74 | C₂H₅ | O | sec-C₄H₉ | H | |
| 2.75 | C₂H₅ | O | tert.-C₄H₉ | H | |
| 2.76 | C₂H₅ | O | –C(CH₃)₂–CH₂–CH₃ | H | |
| 2.77 | C₂H₅ | O | –C(CH₃)₂–CH₂–C(CH₃)₃ | H | |
| 2.78 | C₂H₅ | O | –OH | H | |
| 2.79 | C₂H₅ | O | –OCCH₃ (O) | H | |
| 2.80 | C₂H₅ | O | –O–C(=O)–C₂H₅ | H | |
| 2.81 | C₂H₅ | O | –O–C(=O)–C(CH₃)₃ | H | |

TABLE 2-continued

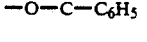

| No. | R¹ | X | R³ | Y | m.p., b.p. [°C.] IR (film), [cm⁻¹] |
|---|---|---|---|---|---|
| 2.82 | C₂H₅ | O | —O—C(=O)—C₆H₅ | H | |
| 2.83 | C₂H₅ | O | —OCH₃ | H | |
| 2.84 | C₂H₅ | O | —OC₂H₅ | H | |
| 2.85 | C₂H₅ | O | —O—C(CH₃)₃ | H | |
| 2.86 | C₂H₅ | O | —CH₂—OH | H | |
| 2.87 | C₂H₅ | O | —CH₂—O—CH₃ | H | |
| 2.88 | C₂H₅ | O | —CH₂—OC₂H₅ | H | |
| 2.89 | C₂H₅ | O | —CH₂—O—C(=O)CH₃ | H | |
| 2.90 | C₂H₅ | O | —CH₂—CH₂—OH | H | |
| 2.91 | C₂H₅ | O | —CH₂—CH₂—C(=O)CH₃ | H | |
| 2.92 | C₂H₅ | O | C₆H₅ | H | |
| 2.93 | C₂H₅ | O | 4-tert.-C₄H₉—C₆H₄ | H | |
| 2.94 | cyclohexyl | O | tert.-C₄H₉ | H | |
| 2.95 | C₆H₅ | O | tert.-C₄H₉ | H | |

Generally speaking, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
Rhizoctonia species in cotton and lawns,
Ustilago species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
*Plasmopara viticola* in grapes,
Alternaria species in vegetables and fruit.

The compounds are applied by spraying or dusting the plants with the active ingredients, or treating the seeds of the plants with the active ingredients. They may be applied before or after infection of the plants or seeds by the fungi. Either the fungi themselves, or the plants, seeds, materials or soil to be protected against fungal attack are treated with a fungicidally effective amount of the active ingredient.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin-sulfite waste liquors and methylcellulose.

The fungicidal agents generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials (wood), for example against *Paecilomyces variotii*.

When the active ingredients are used for treating seed, amounts of from 0.001 to 50, and preferably from 0.01 to 10, g per kg of seed are usually employed.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 1.1 is mixed with 10 parts by weight of N-methyl-α-pyrrolidone. A mixture is obtained which is suitable for application in the form of very fine drops.

II. 20 parts by weight of compound no. 2.5 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 1.1 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 2.5 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 1.1 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 2.5 is intimately mixed with 97 parts by weight of particulate kaolin. A dust is obtained containing 3% by weight of the active ingredient.

VII. 30 parts by weight of compound no. 1.1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 2.5 is intimately mixed with 10 parts by weight of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 1 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

USE EXAMPLES

The compound 8-tert-butyl-2-(piperidino-N-methyl)-1,4-dioxaspiro[4.5]-decane (A) disclosed in EP 281,842 was used for comparison purposes.

USE EXAMPLE 1

Action On Wheat Brown Rust

Leaves of pot-grown wheat seedlings of the "Kanzler" variety were dusted with spores of brown rust (*Puccinia recondita*). The pots were then placed for 24 hours at 20° to 22° C. in a high-humidity (90-95%) chamber. During this period the spores germinated and the germ tubes penetrated the leaf tissue. The infected plants were then sprayed to runoff with aqueous liquors containing (dry basis) 80% of active ingredient and 20% of emulsifier. After the sprayed-on layer had dried, the plants were set up in the greenhouse at 20° to 22° C. and a relative humidity of 65 to 70%. The extent of rust fungus spread on the leaves was assessed after 8 days.

The results show that active ingredients nos. 1.1 and 2.5, applied as 0.006 wt % spray liquors, had a better fungicidal action (100%) than prior art comparative agent A (75%).

USE EXAMPLE 2

Action On Cucumber Mildew

Leaves of pot-grown cucumber seedlings of the "Chinesische Schlange" variety were sprayed at the two-leaf stage with a spore suspension of cucumber mildew. After about 20 hours, the plants were sprayed to runoff with aqueous liquors containing (dry basis) 80% of active ingredient and 20% of emulsifier. After the sprayed-on layer had dried, the plants were set up in the greenhouse at 20°-22° C. and a relative humidity of 70-80%. The extent of fungus spread was determined after 21 days.

The results show that active ingredients nos. 1.1 and 2.5, applied as 0.025% spray liquors, had a better fungicidal action (100%) than prior art comparative agent A (40%).

We claim:

1. A compound selected from the group consisting of compounds of the formula I

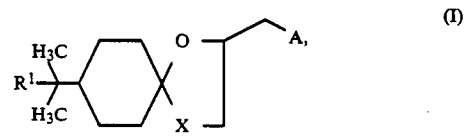

(I)

where
A is a radical II, or III

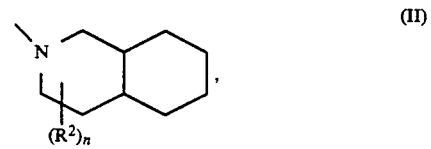

(II)

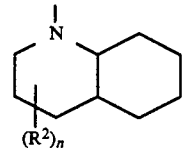

(III)

$R^2$ is $CH_3$, OH or $OCH_3$,
n is from 0 to 3,
X is oxygen, sulfur or methylene, and
$R^1$ is hydrogen, alkyl or unsubstituted or substituted cyclohexyl or unsubstituted or substituted phenyl, and their addition salts with acids.

2. A compound as set forth in claim 1, where
n is 0 or 1,
X is oxygen, sulfur or methylene, and
$R^1$ is hydrogen, straight-chain or branched alkyl of 1 to 6 carbon atoms, phenyl which is unsubstituted or mono- to trisubstituted by identical or different alkyl radicals of 1 to 4 carbon atoms or halogen radicals, or cyclohexyl which is unsubstituted or mono- to trisubstituted by identical or different $C_1$-$C_4$-alkyl or halogen radicals, or its addition salts with acids.

3. A compound of claim 2, wherein A is perhydroquinolino, X is oxygen and $R^1$ is methyl.

4. A fungicidal composition comprising a solid or liquid carrier and a fungicidally effective amount of a compound of the formula I

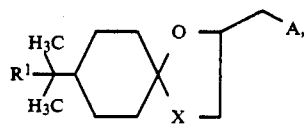
(I)

where
A is a radical II, or III

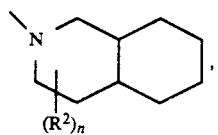
(II)

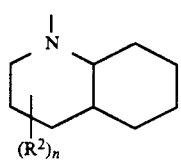
(III)

$R^2$ is $CH_3$, OH or $OCH_3$,
X is oxygen, sulfur or methylene, and
$R^1$ is hydrogen, alkyl or unsubstituted or substituted cyclohexyl or unsubstituted or substituted phenyl, or an addition salt thereof with an acid.

5. A process for combating fungi, wherein a fungicidally effective amount of a compound of the formula I

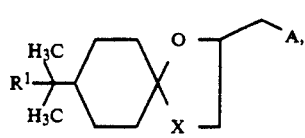
(I)

where
A is a radical II, or III

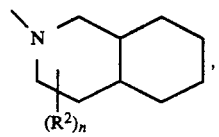
(II)

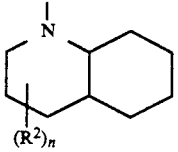
(III)

$R^2$ is $CH_3$, OH or $OCH_3$,
n is from 0 to 3,
X is oxygen, sulfur or methylene, and
$R^1$ is hydrogen, alkyl or unsubstituted or substituted cyclohexyl or unsubstituted or substituted phenyl, or an addition salt thereof with an acid, is applied to the fungi, or the materials, areas, plants or seed threatened by fungus attack.

6. 8-(tert.-Butyl)-2-(perhydroisoquinolinomethyl)-1,4-dioxaspiro[4,5]decane.

7. 8-(Prop-2-yl)-2-(perhydroisoquinolinomethyl)-1,4-dioxaspiro[4,5]decane.

* * * * *